United States Patent [19]

Sembrowich et al.

[11] Patent Number: 5,036,861
[45] Date of Patent: Aug. 6, 1991

[54] METHOD AND APPARATUS FOR NON-INVASIVELY MONITORING PLASMA GLUCOSE LEVELS

[76] Inventors: Walter L. Sembrowich, 6165 Woodchuck Cir., White Bear Lake, Minn. 55110; Carter R. Anderson, 6057 - 67th Way North, Brooklyn Park, Minn. 55429; William R. Kennedy, 2259 Summit Ave., St. Paul, Minn. 55104

[21] Appl. No.: 463,387

[22] Filed: Jan. 11, 1990

[51] Int. Cl.⁵ .................................................. A61B 5/00
[52] U.S. Cl. ........................................ 128/763; 604/20
[58] Field of Search ........................ 128/632, 760, 771; 604/20, 312

[56] References Cited

U.S. PATENT DOCUMENTS

| | | | |
|---|---|---|---|
| 3,964,871 | 6/1976 | Hochstrasser | 23/253 |
| 3,989,036 | 11/1976 | Sasamori | 128/640 |
| 4,190,060 | 2/1980 | Greenleaf et al. | 128/760 |
| 4,197,088 | 4/1980 | Meserol et al. | 424/12 |
| 4,266,556 | 5/1981 | Barlow et al. | 128/760 |
| 4,273,869 | 6/1981 | Shapiro | 435/26 |
| 4,329,999 | 5/1982 | Phillips | 128/760 |
| 4,383,529 | 5/1983 | Webster | 604/20 |
| 4,397,956 | 8/1983 | Maggio | 436/34 |
| 4,400,353 | 8/1983 | Meserol et al. | 422/73 |
| 4,406,658 | 9/1983 | Lattin et al. | 604/20 |
| 4,411,518 | 10/1983 | Meserol et al. | 356/39 |
| 4,457,748 | 7/1984 | Lattin et al. | 604/20 |
| 4,532,937 | 8/1985 | Miller | 128/759 |
| 4,542,751 | 9/1985 | Webster et al. | 128/760 |
| 4,595,011 | 6/1986 | Phillips | 128/760 |
| 4,635,488 | 1/1987 | Kremer | 128/760 |
| 4,689,309 | 8/1987 | Jones | 436/95 |
| 4,706,676 | 11/1987 | Peck | 128/760 |
| 4,707,438 | 11/1987 | Keydar | 435/5 |
| 4,732,153 | 3/1988 | Phillips | 128/760 |
| 4,734,090 | 3/1988 | Sibalis | 604/20 |
| 4,744,787 | 5/1988 | Phipps et al. | 604/20 |
| 4,771,059 | 9/1988 | Bodor | 514/355 |
| 4,805,623 | 2/1989 | Jobsis | 128/633 |
| 4,810,470 | 3/1989 | Burkhardt et al. | 422/56 |
| 4,819,645 | 4/1989 | Peck | 128/760 |
| 4,821,733 | 4/1989 | Peck | 128/760 |
| 4,824,850 | 4/1989 | Bodor | 514/370 |
| 4,828,716 | 5/1989 | McEwen et al. | 210/740 |
| 4,829,070 | 5/1989 | Bodor | 514/307 |
| 4,834,101 | 5/1989 | Collison et al. | 128/635 |

OTHER PUBLICATIONS

*Iontophoretic Delivery of Drugs: Fundamentals, Developments and Biomedical Applications*, by Ajay K. Banga and Yie W. Chien, Jan. 1988.
*The Effects of Ouabain on Eccrine Sweat Gland Function*, by Kenzo Sato, M.D., J. Richard Taylor, M.D. and Richard L. Dobson, M.D., Jan. 1969.
*The Physiology and Pharmacology of the Eccrine Sweat Gland*, by Kenzo Sato, Jan. 1983.
*Sweat Induction from and Isolated Eccrine Sweat Gland*, by Kenzo Sato, Nov. 1973.
*The Physiology, Pharmacology of the Eccrine Sweat Gland*, by Kenzo Sato, Jan. 1979.

Primary Examiner—Max Hindenburg
Attorney, Agent, or Firm—Kinney & Lange

[57] ABSTRACT

A method and apparatus non-invasively monitor plasma constituent levels. A localized, modified sweating response is induced providing a sweat secretion for analysis of the plasma constituents.

53 Claims, 3 Drawing Sheets

METHOD AND APPARATUS FOR NON-INVASIVELY MONITORING PLASMA GLUCOSE LEVELS

BACKGROUND OF THE INVENTION

The present invention relates generally to the non-invasive monitoring of plasma glucose levels by inducing localized sweating which produces a glucose-containing sweat sample.

The monitoring of plasma glucose levels in patients is of major importance in the field of medicine in terms of diagnosis, health maintenance, and management of disease. Typically, plasma constituents, such as glucose, are monitored by removing a blood sample from the patient and analyzing the blood sample. This involves an invasive procedure, such as finger pricking or entering a vein with a syringe to remove the blood. These invasive procedures can be painful and inconvenient, especially for a self-testing patient.

Non-invasive technology is employed in a number of medical contexts. Medical iontophoresis is a procedure whereby electric current is employed to transdermally mobilize ionic medicaments. Pharmacologic agents can thereby be introduced into the patient, without invasion of the patient. Non-invasive technology is also employed in the diagnosis of certain disease states. For example, it is well known that the sweat of a patient suffering from cystic fibrosis contains elevated levels of chloride. Medical iontophoresis is employed to pharmacologically stimulate a sweating response using a test patch containing a sweat-inducing agent. The test patch collects the sweat and is then used to provide sweat for analysis of the chloride level in the sweat sample. This technique is described in detail in the Lattin et al. U.S. Pat. No. 4,457,748. Thus, the nonsweating through iontophoresis allows for the diagnosis of cystic fibrosis through the analysis of the chloride level in a sweat sample.

However, there is presently no technology available for the non-invasive monitoring of plasma constituents, such as glucose. Eccrine sweat contains many compounds of interest, but there is typically no glucose present in a sample of eccrine sweat on the skin surface. Although glucose may present in the secretory coil of the eccrine sweat gland in equilibrium with plasma glucose levels, that glucose is depleted as the sweat moves to the skin surface.

Therefore, there is a continuing need for improved non-invasive technologies for monitoring important constituents present in the plasma of a patient.

SUMMARY OF THE INVENTION

The present invention is a method and apparatus for non-invasively monitoring plasma constituent levels. A localized sweating response is induced. The sweat is then analyzed for the constituent.

In one preferred embodiment of the present invention, the sweat is pharmacologically modified to contain the constituent (e.g. glucose). The sweat then is collected and the glucose concentration is simultaneously measured.

Also, in a preferred embodiment of the present invention, the localized sweating response is induced via the heating of a localized area of the skin. Alternatively, the localized sweating response can be induced pharmacologically and non-invasively.

DETAILED DESCRIPTION OF THE PREFERRED EMBODIMENTS

Figure 1:
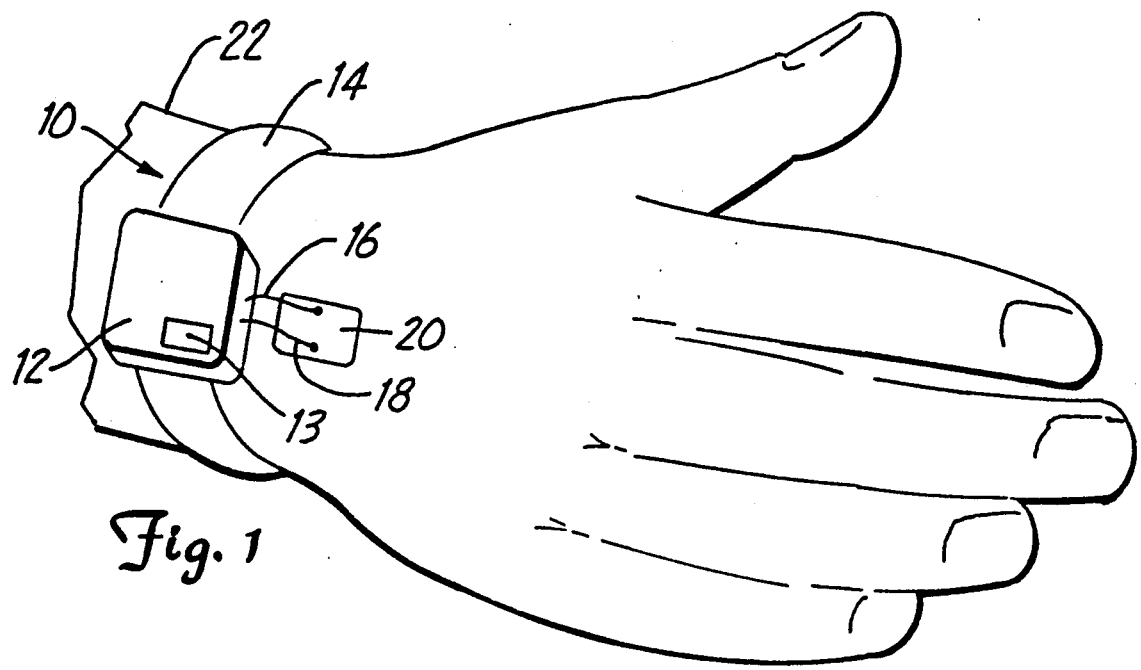
FIG. 1 is a drawing of the glucose monitor of the present invention.

FIG. 1 is a drawing of monitor 10. Although the present invention is suitable for monitoring any number of sweat constituents, for simplicity's sake, it will be described primarily in the context of a glucose monitor. Glucose monitor 10 is comprised of supply 12 (which includes start button 13), strap 14, conductors 16 and 18 and skin patch 20. Strap 14 is attached to supply 12. Glucose monitor 10 is shown attached to a human wrist 22 via strap 14. Skin patch 20 is provided with a pharmacologic solution which, when transdermally introduced into wrist 22, stimulates the secretion mechanism in the eccrine sweat gland. The pharmacological solution also contains a sweat modifying agent which modifies the sweat secretion process so that sweat appearing at the surface of the skin contains glucose in a quantity at equilibrium with that contained in plasma.

When skin patch 20 is brought into contact with wrist 22, an operator presses start button 13. When start button 13 is pressed, supply 12 supplies an electric current to skin patch 20 through conductors 16 and 18. Applying a direct current to skin patch 20 causes the pharmacologic solution to be transdermally introduced into wrist 22. The technique of non-invasively transdermally introducing chemicals into the body through application of a direct current is well known in the art and is referred to as iontophoresis.

Once introduced, the pharmacologic solution stimulates sweat in the eccrine sweat gland and preserves glucose levels in the secretion as the secretion moves to the skin surface through the lumen of the gland. Once the sweat reaches the skin surface, skin patch 20 is removed and the sweat is collected and analyzed for glucose level.

Figure 2:
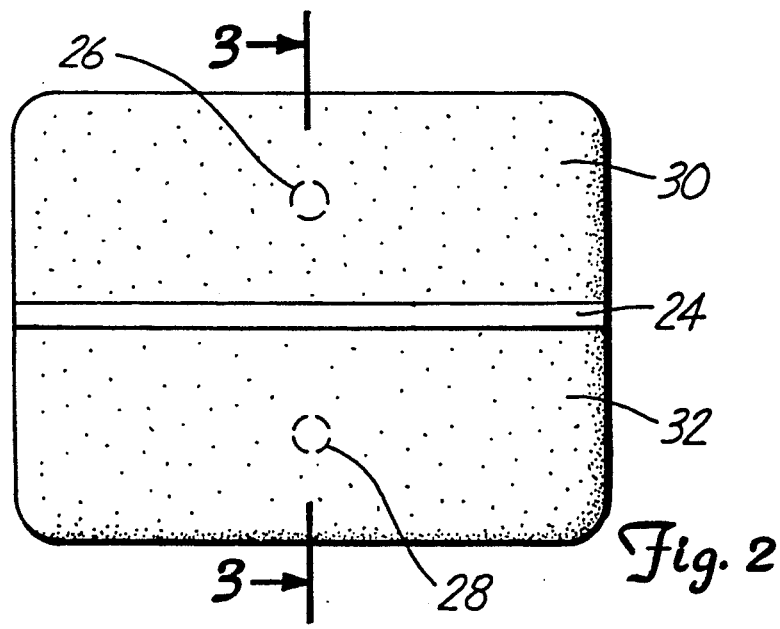
FIG. 2 is a bottom view of a skin patch.

FIG. 2 is a bottom view of skin patch 20. Skin patch 20 includes separator 24 for separating the pharmacologic solutions and electrodes 26 and 28. Electrodes 26 and 28 are covered with patches 30 and 32 containing pharmacologic solutions. Therefore, electrodes 26 and 28 are shown in phantom in FIG. 2. Electrodes 26 and 28 are also connected to supply 12 via conductors 16 and 18 shown in FIG. 1.

Figure 3:
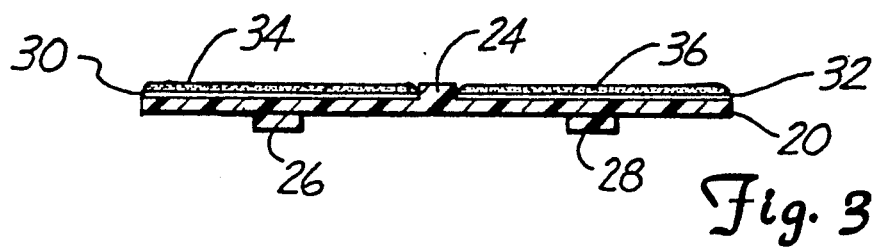
FIG. 3 is a sectional view of the skin patch taken along lines 3—3 in FIG. 2.

FIG. 3 is a sectional view of skin patch 20 taken along line 3—3 of FIG. 2. Pharmacologic gel 34 is applied to strip 30 and pharmacologic gel 36 is applied to strip 32. Gel 34 is the iontophoretic gel which is transdermally introduced into wrist 22. Gel 36 is a reference gel such as a salt solution or potassium sulphate.

When iontophoresis is used to transdermally introduce gel 34, gel 34 contains a cholinergic agent such as pilocarpine for stimulating the secretion mechanism in the eccrine sweat gland. Gel 34 also contains agents which, when transdermally introduced, modify the sweat gland secretion mechanism so that the secretion appearing at the surface of the skin contains glucose which is preserved in the sweat at levels in equilibrium with (or in a known relationship to) those found in plasma.

Glucose is thought to be the energy source for a secreting eccrine sweat gland. Therefore, as the sweat gland pumps sweat to the skin surface, it removes the glucose from the sweat and uses it as an energy source. Hence, it is necessary to provide the eccrine sweat gland with an exogenous source of energy to preserve the glucose secreted by the sweat gland. An example of such a compound is glucose-6-phosphate Therefore, glucose-6-phosphate, in one preferred embodiment, is used as the energy supplier in pharmacologic gel 34.

Glucose is also thought to be reabsorbed along duct cells of the eccrine sweat gland as it moves toward the skin surface. Therefore, the use of a glucose transport inhibitor in gel 34 preserves the glucose levels in the sweat gland secretion as it moves through the lumen in the gland tubule. In one preferred embodiment, the glucose transport inhibitor used in gel 34 is phlorizin.

It should also be noted that if the desired constituent to be monitored is something other than glucose (for example, sodium) a substitute agent may be required for glucose-6-phosphate and phlorizin in gel 34. For instance, as the eccrine sweat gland pumps sodium out of cytoplasm and into the secretory coil, an ultrafiltrate secretion results which is a plasma-like isotonic fluid. As this fluid moves along the lumen of the sweat gland tubule, sodium transport proteins pump sodium out of the lumen and back into the interstitial space. Hence, a sodium transport inhibitor would be added to gel 34 to block the re-uptake of sodium into the interstitial fluid. This preserves the isotonicity of the sweat appearing at the skin surface. One example of such a sodium transport inhibitor is ouabain.

An example of gel 34 used in monitoring glucose is a gel containing 1% by weight pilocarpine, glucose-6-phosphate at 1 millimolar concentration and phlorizin at 0.1% by weight. If sodium is to be monitored, gel 34, in one preferred embodiment, contains 1% by weight pilocarpine and 0.1% by weight ouabain.

Once gel 34 is transdermally introduced into wrist 22 by using iontophoresis, a localized sweating response is induced in the area under skin patch 20. The secretion provided is modified by the agents described above so that the glucose levels reflect those found in plasma. The sweat can then be collected and analyzed to determine glucose levels.

Figure 4:
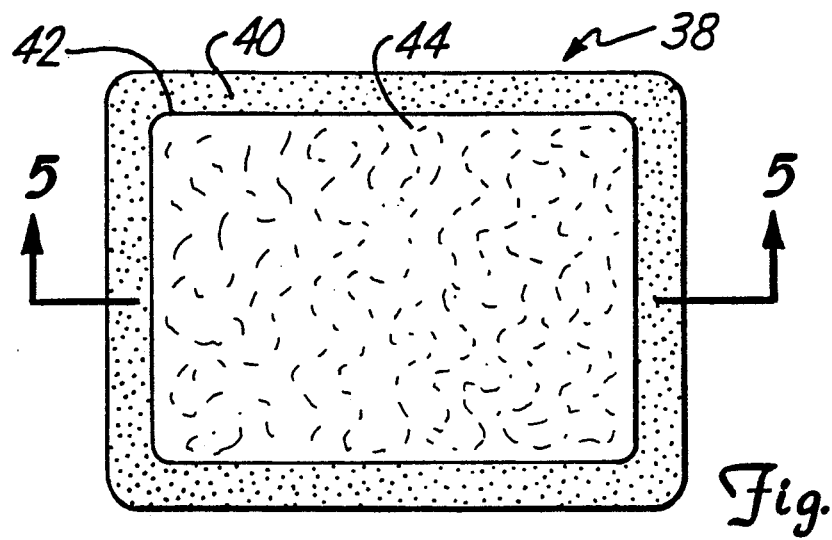
FIG. 4 is a bottom view of another preferred embodiment of a skin patch.
Figure 5:
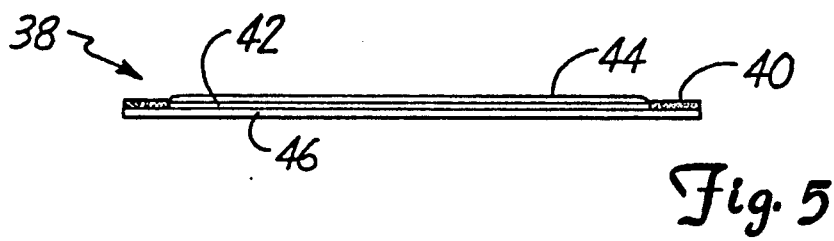
FIG. 5 is a sectional view of the skin patch taken along line 5—5 in FIG. 4.

FIG. 4 is another preferred embodiment of a skin patch for producing a modified sweating response. FIG. 4 is a bottom view of skin patch 38. Skin patch 38 includes an adhesive boundary 40 as well as a collector pad 42 which is shown with a skin penetration compound 44 applied to it. Skin penetration compound 44 includes all of the agents included in iontophoretic gel 34. However, skin penetration compound 44 (gel 44) is not transdermally introduced into wrist 22 through iontophoresis. Rather, skin penetration enhancers are added to gel 44 so that it is transdermally introduced into wrist 22 without any electric current being applied. One preferred skin penetration enhancer is dimethyl-sulfoxide (DMSO). DMSO is added at approximately 50% by volume to gel 34 to produce gel 44.

Also, as skin penetration compound 44 is transdermally introduced into wrist 22, and as sweat is stimulated and brought to the skin surface under skin patch 38, collector pad 42 absorbs the sweat appearing at the skin surface. After a desired time interval, collector pad 42 is simply removed from substrate 46 and analyzed to determine glucose levels.

Figure 6:
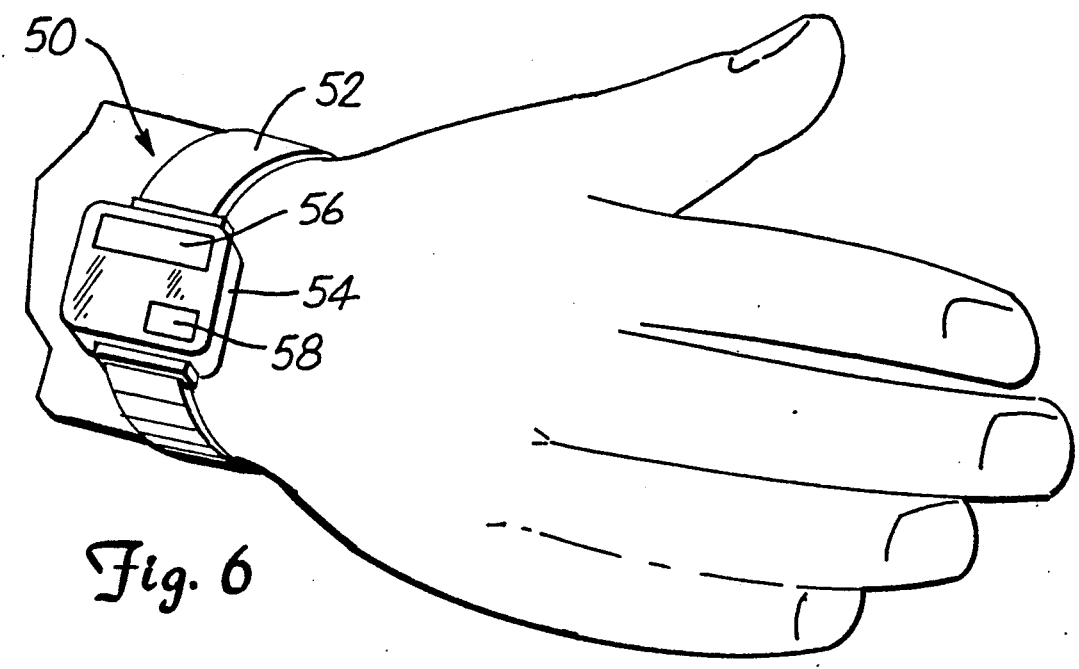
FIG. 6 is a drawing of a second embodiment of the glucose monitor of the present invention.
Figure 7:
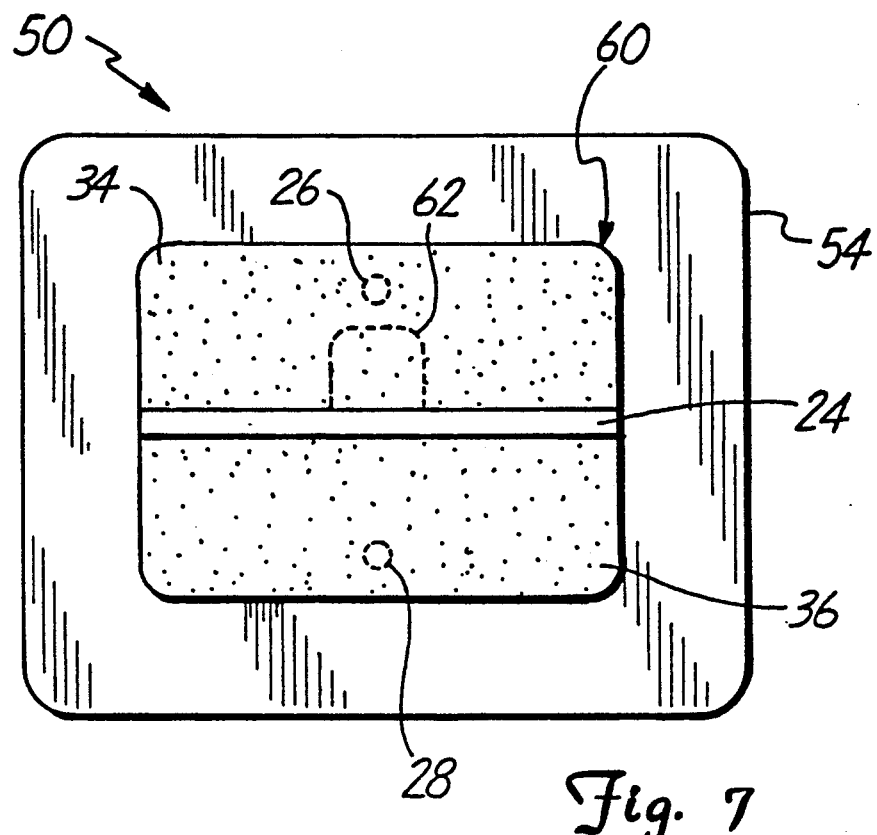
FIG. 7 is a bottom view of the glucose monitor shown in FIG. 6.

FIG. 6 is a preferred embodiment of integral glucose monitor 50 which both induces localized sweating and analyzes the sweat sample produced. Integral glucose monitor 50 includes strap 52, electronic unit 54, display 56 and start button 58. FIG. 7 shows a bottom view of glucose monitor 50. FIG. 7 shows that electronic unit 54 is provided with skin patch 60 which is substantially identical to skin patch 20 shown in FIGS. 1-3. The only difference between skin patch 20 and skin patch 60 is that skin patch 60 is provided with glucose monitoring electrode 62.

Figure 8:
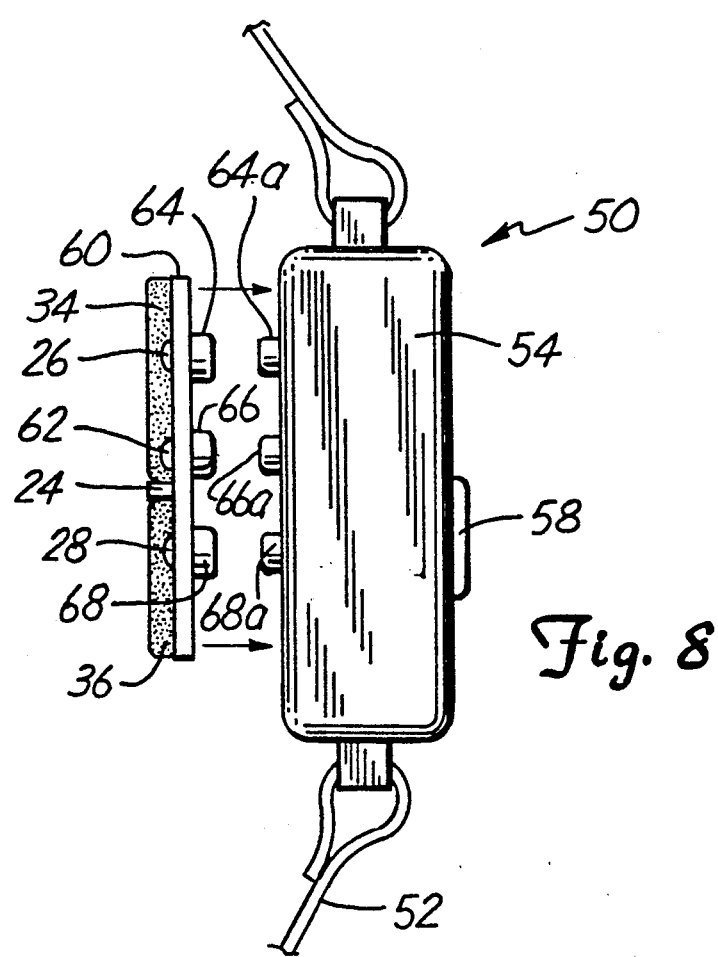
FIG. 8 is an exploded side view of the glucose monitor shown in FIG. 6.

FIG. 8 is an exploded side view of glucose monitor 50. Electronic unit 54 and skin patch 60 are provided with electric snap connectors 64, 64A, 66, 66A, 68 and 68A. Electric snap connectors 64 and 64A provide an electrical connection between electronic unit 54 and stimulating electrode 26. Therefore, connectors 64 and 64A effectively take the place of conductor 16 in the embodiment shown in FIG. 1.

Similarly, electric snap connectors 68 and 68A provide an electrical connection between electronic unit 54 and reference electrode 28. Hence, connectors 68 and 68A effectively function the same as conductor 18 in FIG. 1.

As in the embodiment shown in FIG. 1, when the operator depresses start button 58, the active components of gel 34 are transdermally introduced into wrist 22 through iontophoresis. As gel 34 is transdermally introduced and stimulates the sweating mechanism in the localized area under skin patch 60, and as the induced, modified secretion reaches the skin surface, it comes into contact with glucose measuring electrode 62. Glucose measuring electrode 62, can be any device which produces a measurable response which varies with the concentration of glucose it is exposed to. Hence, glucose measuring electrode 62 produces a glucose signal representative of the concentration of glucose present in the sweat at the skin surface and provides that signal to electronic unit 54 via connectors 66 and 66A. Electronic unit 54 receives the glucose signal, determines the glucose level and displays the glucose level at display 56 (shown in FIG. 6).

It should be noted that the technique of using pilocarpine to induce a sweating response could be replaced with a technique of using a localized heater to induce a localized sweating response or with any other suitable sweat-inducing technique.

CONCLUSION

The method and apparatus of the present invention non-invasively stimulates the sweating mechanism in the eccrine sweat gland in a localized area and produces a discrete sample of sweat at the skin surface. The sweating mechanism in the localized area is pharmacologically modified so that glucose or sodium or other desired constituent levels are maintained in the sweat at a level in equilibrium with that at which they are found in plasma.

Where glucose is the constituent being monitored, an agent is introduced, simultaneously with the inducement of the sweating response, which blocks glucose reabsorption from the sweat. Other agents are also introduced which supply energy for the secreting sweat gland. This produces a sample of sweat at the skin surface in the localized area which contains analytically significant glucose levels. The sweat is then analyzed immediately upon its appearance at the skin surface or collected and analyzed at a later time.

It should be noted that this invention may be used for non-invasively monitoring the levels of any clinically important plasma constituent such as sodium. The present invention produces a collectable sample of sweat at the skin surface which contains constituents in equilibrium with their plasma counterparts. This technique does not involve invasion of the body and provides a clear analytic sample which may be completely aviral.

Although the present invention has been described with reference to preferred embodiments, workers skilled in the art will recognize that changes may be made in form and detail without departing from the spirit and scope of the invention.

What is claimed is:

1. A method of non-invasively monitoring a constituent in the plasma of a patient, the method comprising:
    non-invasively inducing a localized sweating response;
    non-invasively introducing an agent causing the constituent to appear in sweat secretions;
    collecting a discrete sample of pharmacologically-induced sweat, containing the constituent, at a skin surface; and
    monitoring a characteristic of the constituent in the sample.

2. The method of claim 1 wherein non-invasively inducing a localized sweating response includes heating a localized area of skin.

3. The method of claim 1 wherein non-invasively inducing a localized sweating response includes mobilizing a first pharmacologic agent transdermally via medical iontophoresis.

4. The method of claim 3 wherein the first pharmacologic agent is a cholinergic agent.

5. The method of claim 1 wherein the constituent is glucose.

6. The method of claim 5 wherein the step of non-invasively introducing an agent causing the constituent to appear in sweat secretions further comprises the step of:
    non-invasively introducing a pharmacologic agent which blocks glucose reabsorption from sweat.

7. The method of claim 6 and further comprising the step of:
    non-invasively introducing a pharmacologic agent which provides an energy supply for secreting sweat glands.

8. The method of claim 7 wherein the pharmacologic agent which blocks glucose reabsorption includes phlorizin and the pharmacologic agent which provides an energy supply includes glucose-6-phosphate.

9. A method for non-invasively monitoring plasma glucose levels in a patient, the method comprising:
    non-invasively inducing a localized sweating response, introducing a first pharmacologic agent which blocks glucose reabsorption by the sweat gland, and introducing a second pharmacologic agent non-invasively which provides an energy supply for the secreting sweat gland;
    collecting a discrete sample of pharmacologically-modified sweat, containing glucose, at the surface of the skin; and
    determining a plasma glucose level based upon the glucose contained in the sample.

10. The method of claim 9 wherein non-invasively inducing a localized sweating response includes heating a localized area of the skin.

11. The method of claim 9 wherein non-invasively inducing a localized sweating response includes mobilizing a third pharmacologic agent transdermally via medical iontophoresis.

12. The method of claim wherein the third pharmacologic agent is a cholinergic agent.

13. The method of claim 9 and wherein non-invasively introducing the first and second pharmacologic agents includes transdermally mobilizing the agents via medical iontophoresis.

14. The method of claim 9 and wherein the first agent which blocks glucose reabsorption includes phlorizin.

15. The method of claim 9 and wherein the second agent which provides an energy supply includes glucose-6-phosphate.

16. A method of non-invasively monitoring a concentration of a constituent in plasma of a patient, the method comprising:
    stimulating sweat secretion in a localized area of the patient's body;
    modifying sweat gland secretion in the localized area so that a concentration of the constituent in sweat secreted in the localized area has a known relationship to the concentration of the constituent in the plasma; and
    measuring concentration of the constituent in a sample of sweat secreted in the localized area.

17. The method of claim 16 wherein stimulating sweat secretion comprises heating a localized area of the skin.

18. The method of claim 16 wherein stimulating sweat secretion comprises introducing transdermally a first pharmacologic agent which induces a localized sweating response.

19. The method of claim 18 wherein the first pharmacologic agent includes pilocarpine.

20. The method of claim 16 wherein modifying sweat gland secretion comprises introducing transdermally a second pharmacologic agent which blocks glucose reabsorption from sweat.

21. The method of claim 20 wherein the constituent is glucose.

22. The method of claim 20 wherein the second pharmacologic agent includes phlorizin.

23. The method of claim 20 wherein introducing an agent further comprises introducing transdermally a third pharmacologic agent which provides an energy supply for secreting sweat glands.

24. The method of claim 23 wherein the third pharmacologic agent includes glucose-6-phosphate.

25. The method of claim 16 wherein measuring concentration comprises:
    collecting a sample of sweat secreted in the localized area; and
    measuring concentration of the constituent in the sample collected.

26. An apparatus for non-invasively monitoring a constituent in the plasma of a patient, comprising:

an inducer for non-invasively inducing a localized sweating response;

a modifier for non-invasively modifying the sweating response to make the constituent appear in sweat secretions;

a collector for collecting a discrete sample of pharmacologically-induced sweat, containing the constituent, at a skin surface; and a monitor for monitoring a characteristic of the constituent in the sample.

27. The apparatus of claim 26 wherein the inducer comprises:

a heater for heating a localized area of skin.

28. The apparatus of claim 26 wherein the inducer comprises:

a mobilizer for mobilizing a first pharmacologic agent transdermally via medical iontophoresis.

29. The apparatus of claim 28 wherein the first pharmacologic agent is a cholinergic agent.

30. The apparatus of claim 26 wherein the constituent is glucose.

31. The apparatus of claim 30 and further comprising:

a first introducer for non-invasively introducing a second pharmacologic agent which blocks glucose reabsorption from sweat.

32. The apparatus of claim 31 and further comprising:

a second introducer for non-invasively introducing a third pharmacologic agent which provides an energy supply for secreting sweat glands.

33. The apparatus of claim 32 wherein the second pharmacologic agent comprises:

phlorizin and the third pharmacologic agent comprises glucose-6-phosphate.

34. An apparatus for non-invasively monitoring plasma glucose levels in a patient, comprising:

an inducer for non-invasively inducing a localized sweating response, introducing a first pharmacologic agent non-invasively which blocks glucose reabsorption by the sweat gland, and for introducing a second pharmacologic agent non-invasively which provides an energy supply for the secreting sweat gland.

35. The apparatus of claim 34 and further comprising:

a collector for collecting a discrete sample of pharmacologically-modified sweat, containing glucose, at the surface of the skin.

36. The apparatus of claim 35 and further comprising:

a glucose level determining device for determining a plasma glucose level based upon the glucose combined in the sample.

37. The apparatus of claim 34 wherein the inducer comprises a heater for heating a localized area of the skin.

38. The apparatus of claim 34 wherein the inducer comprises:

a mobilizer for mobilizing a third pharmacologic agent transdermally via medical iontophoresis.

39. The apparatus of claim 38 wherein the third pharmacologic agent is a cholinergic agent.

40. The apparatus of claim 34 wherein the first and second pharmacologic agents are introduced by transdermally mobilizing the agent via medical iontophoresis.

41. The apparatus of claim 34 wherein the first agent which blocks glucose reabsorption includes phlorizin.

42. The apparatus of claim 34 wherein the second pharmacologic agent which provides an energy supply includes glucose-6-phosphate.

43. An apparatus for non-invasively monitoring a concentration of a constituent in plasma of a patient, comprising:

a stimulator for stimulating sweat secretion in a localized area of patient's body; and a modifier for modifying sweat gland secretion in the localized area so that a concentration of the constituent in sweat secreted in the localized area has a known relationship to the concentration of the constituent in the plasma.

44. The apparatus of claim 43 and further comprising:

a measurement device for measuring concentration of the constituent in a sample of sweat secreted in the localized area.

45. The apparatus of claim 44 wherein the measurement device comprises:

a collector for collecting a sample of sweat secreted in the localized area; and a measuring device for measuring concentration of the constituent in the sample collected.

46. The apparatus of claim 43 wherein the stimulator comprises:

a heater for heating a localized area of the skin.

47. The apparatus of claim 43 wherein the stimulator comprises:

a transdermal introducer for transdermally introducing a fist pharmacologic agent which induces a localized sweating response.

48. The apparatus of claim 47 wherein the first pharmacologic agent includes pilocarpine.

49. The apparatus of claim 43 wherein the modifier comprises:

a transdermal introducer for transdermally introducing a second pharmacologic agent which blocks glucose reabsorption from sweat.

50. The apparatus of claim 49 wherein the constituent is glucose.

51. The apparatus of claim 48 wherein the second pharmacologic agent includes phlorizin.

52. The apparatus of claim 49 wherein the transdermal introducer comprises a second transdermal introducer for introducing transdermally a third pharmacologic agent which provides an energy supply for secreting sweat glands.

53. The apparatus of claim 51 wherein the third pharmacologic agent includes glucose-6-phosphate.

* * * * *

UNITED STATES PATENT AND TRADEMARK OFFICE
CERTIFICATE OF CORRECTION

PATENT NO. : 5,036,861
DATED : August 6, 1991
INVENTOR(S) : Walter L. Sembrowich et al.

It is certified that error appears in the above-identified patent and that said Letters Patent is hereby corrected as shown below:

Col. 6, line 15, delete "claim", insert --claim 11--.

Col. 8, line 49, delete "claim 48", insert --claim 49--.

Col. 8, line 56, delete "claim 51", insert --claim 52--.

Signed and Sealed this

Twenty-ninth Day of December, 1992

Attest:

DOUGLAS B. COMER

*Attesting Officer*     Acting Commissioner of Patents and Trademarks